United States Patent [19]

Cleveland et al.

[11] Patent Number: 4,629,806

[45] Date of Patent: Dec. 16, 1986

[54] VAPOR STATE FORMATION OF DIESTERS OF OXALIC ACID

[75] Inventors: Thomas C. Cleveland, Dunbar; James E. Deitzler, South Charleston; Arthur R. Doumaux, Jr., Charleston; Joseph P. Henry, South Charleston; John M. Hurt, St. Albans; Louis A. Kapicak; Bernard C. Ream, both of Charleston, all of W. Va.

[73] Assignee: Union Carbide Corporation, New York, N.Y.

[21] Appl. No.: 239,763

[22] Filed: Mar. 12, 1981

Related U.S. Application Data

[63] Continuation-in-part of Ser. No. 227,793, Jan. 23, 1981, abandoned.

[51] Int. Cl.$^4$ ............................................. C07C 67/36

[52] U.S. Cl. .................................... 560/204; 502/152; 502/327; 560/190

[58] Field of Search ........................ 560/204; 252/472

[56] References Cited

U.S. PATENT DOCUMENTS 4,138,587 2/1979 Yamasaki et al. .................. 560/204
4,229,591 10/1980 Nishimura et al. ................. 560/204

*Primary Examiner*—Natalie Trousof
*Assistant Examiner*—Vera C. Clarke
*Attorney, Agent, or Firm*—James C. Arvantes; George A. Skoler; Gary L. Wamer

[57] ABSTRACT

A continuous vapor state process for the preparation of diesters of oxalic acid from a nitrogen oxide, an alcohol and carbon monoxide.

26 Claims, 2 Drawing Figures

VAPOR STATE FORMATION OF DIESTERS OF OXALIC ACID

This application is a continuation-in-part of U.S. Ser. No. 227,793, filed Jan. 23, 1981, commonly assigned, now abandoned.

FIELD OF THE INVENTION

This process relates to a novel vapor state process for the preparation of diesters of oxalic acid from a nitrogen oxide, an alcohol and carbon monoxide. (The terms "vapor state" and "vapor phase" are used interchangeably to refer to a process carried out in the gaseous phase.)

BACKGROUND OF THE INVENTION

The preparation of diesters of oxalic acids (oxalates) is of particular interest to the chemical industry owing to the varied uses of these compounds. Not only may these diesters serve to act as the starting materials for such important compounds as oxalic acid, oxamide or ethylene glycol, but they may also find extensive use as intermediates for dyes, pharmaceuticals and the like.

Prior to the instant invention there have been proposed conventional liquid phase processes for the formation of these diesters which employ various catalyst systems, co-catalysts, reaction accelerators and the like. However, these conventional processes have suffered from the serious effects arising from conventional liquid phase processes.

A particularly interesting process for preparing diesters of oxalic acid in the liquid phase is disclosed in U.S. Pat. No. 4,138,587. U.S. Pat. No. 4,138,587 employs nitric acid or a nitrogen oxide as the accelerator in the presence of a solid platinum group metal or salt thereof, alcohol, molecular oxygen and carbon monoxide. The process is a liquid phase process and suffers from significant practical defects related to liquid phase processes, such as catalyst losses, large by-product formation, low efficiencies to product, to name a few.

U.S. Pat. No. 4,229,591 discloses, in part, a vapor phase process. The process disclosed therein involves contacting an ester of nitrous acid with carbon monoxide in the gaseous phase under ordinary pressure in the presence of a solid catalyst containing metallic palladium or a salt thereof at a temperature of 50° to 200° C., in which the ester of nitrous acid is an ester of nitrous acid with an alcohol having 1 to 8 carbon atoms such as saturated monohydric aliphatic alcohols and alicyclic alcohols. Although this process provides advantages over the corresponding liquid phase process, the vapor phase process does not provide a completely vapor phase process in which the alkyl nitrite is also prepared in the vapor state in a separate step. An exception described in this patent involves nitrite formation in situ in the oxalate reactor concurrent with oxalate formation. Such in situ formation adds a potential hazardous procedure and introduces water into the reactor in amounts which affect the production of significant quantities of undesirable by-products.

Japanese Application No. 53-8268/78 describes the preparation of nitrite esters by conventional liquid phase processes as part of the continuous production of oxalic acid diester using nitrite ester as a starting material by the vapor phase oxalate process of U.S. Pat. No. 4,229,591. The nitrous acid ester is formed by employing a gas-liquid contacting apparatus to contact a gaseous nitrogen oxide mixture with liquid alcohol at a temperature lower than the boiling point of the alcohol.

There is foreseen herein an advantage of having a multi-step wholly vapor phase process where the presence of undesirable amounts of water in the oxalate reaction can be avoided. For example, effecting the process in two vapor phase reaction zones both greatly improves the conversion of reactants to desired product (the diester of oxalic acid) and minimizes by-product formation. Other advantages are achieved, such as enhancement of catalyst life, due to minimization of deleterious by-products which can attack the catalyst either to dissolve a portion of it or to form stable and unreactive species.

In order to have a "true" vapor state process the entire process must be effected in the vapor state and, further, if the process is to be optimized, the nitrite formation should be in a reaction zone apart from the oxalate forming reaction zone. In the present process, because the ester of nitrous acid is prepared in the vapor state in a nitrous ester forming reaction zone the overall process minimizes by-product formation, enhances catalyst life, provides higher conversions to and yields of the diester of oxalic acid, and the like. By correlating the process steps so as to have an integrated vapor state process, i.e., have the formation of both the ester of nitrous acid and the diester of oxalic acid in the vapor state, in nitrous acid ester forming and oxalate forming reaction zones, respectively, an optimized process is obtained.

The classical method for preparing nitrite esters involves the liquid phase reaction of sodium nitrite and sulfuric acid with a desired alcohol. The reaction is normally carried out at ice temperatures, due to the extremely exothermic nature of the reaction, to form nitrite ester as follows:

$$2NaNO_2 + H_2SO_4 + 2ROH \rightarrow 2RONO + Na_2SO_4 + 2H_2O$$

The nitrite ester formed is essentially insoluble in water (less than about 1 percent in water or water in the nitrite ester) so that the nitrite ester is separated from the reaction products by liquid separation.

The production of nitrite esters in the liquid phase is disclosed in U.S. Pat. No. 2,166,698 wherein nitrite esters are produced by reacting an appreciably water soluble saturated open-chain aliphatic compound containing a plurality of esterifiable carbinol groups with nitrous acid in an aqueous medium and removing a nitrite ester from the reaction system substantially as soon as it is formed therein. The nitrite esters formed therein react rapidly with alcohols, e.g., ethyl alcohol, to form alkyl nitrites, e.g., ethyl nitrite.

In U.S. Pat. No. 2,739,166 alkyl nitrites are produced in a liquid phase process by bubbling nitrogen dioxide gas into a cooled liquid monohydric aliphatic alcohol.

In British Patent Specification No. 586,022 a liquid phase process is disclosed for the preparation of nitric acid esters which comprises reacting an alcohol with dinitrogen tetroxide in the liquid phase.

In German Patentschrift No. 1,156,775 a liquid phase process is disclosed for preparing esters of nitrous acid by employing alcohol in molar excess over dinitrogen trioxide at temperatures below the boiling point of the alcohol and simultaneously distilling off the ester formed. In addition, the reference acknowledges that the vapor phase decomposition of alcohols with nitrogen dioxide-nitrogen monoxide mixtures at temperatures between 100° and 420° C. is known.

The aforementioned processes are to be distinguished from a vapor phase process that may be employed in the process of this invention in that in the liquid phase processes the separation of the nitrite ester product is difficult and oxidation of alcohol in the liquid phase during the manufacture or separation can occur to form unwanted by-products. In addition, the separation of the highly flammable and toxic nitrite ester from the liquid phase can prove to be a major safety and health problem. The resulting ester of nitrous acid can be obtained only after separation and purification.

A vapor phase process for the preparation of ester of nitrous acid is disclosed in U.S. Pat. No. 2,831,882. The patent's process comprises reacting a vaporized alcohol with from 0.4 to 0.6 mole of nitrogen dioxide and 0.4 to 2.0 moles of nitric oxide per mole of alcohol in the presence of from 2 to 25 moles of diluent selected from the group consisting of water, nitrogen, and carbon dioxide at a temperature between 100° C. and 420° C. with a contact time of 1–10 seconds.

SUMMARY OF THE INVENTION

The process of this invention involves the preparation of diesters of oxalic acid which comprises contacting a nitrogen oxide and an alcohol having 1 to 8 carbon atoms, such as a saturated monohydric aliphatic alcohol, in the vapor state in a nitrous ester forming reaction zone for a sufficient time to form the ester of nitrous acid; maintaining the ester of nitrous acid in the vapor state and contacting said ester of nitrous acid, preferably after the removal of deleterious water, with carbon monoxide in the vapor state in an oxalate forming reaction zone, at a temperature of between about 50° C. and 200° C., over a supported palladium containing catalyst in which the palladium is metallic palladium or a salt thereof, to produce the diester of oxalic acid. Preferably, the process is operated continuously and as a cyclic process wherein there exists at least one cycle (recycle) gas stream.

DETAILED DESCRIPTION

The present process relates to a wholly vapor state process for the preparation of diesters of oxalic acid. The process is carried out in the vapor state in two correlated steps: the first step comprises the vapor state formation in a nitrous ester forming reaction zone of an ester of nitrous acid; and the second step comprises the reaction of an ester of nitrous acid and carbon monoxide in the vapor state in an oxalate forming reaction zone over a supported palladium catalyst. In addition, the process provides for the removal of deleterious amounts of water formed in the first step prior to introducing the ester of nitrous acid to the aforementioned second step.

The esters of nitrous acid may be formed by most any vapor state synthetic scheme from a nitrogen oxide gas and vaporous alcohol which provides an ester of nitrous acid in the vapor state in the reaction system. Exemplary of such nitrogen oxides are nitrogen monoxide (nitric oxide), nitrogen dioxide, dinitrogen trioxide, dinitrogen tetroxide, and hydrates of the aforementioned. In the case where nitrogen monoxide (nitric oxide) is employed it is necessary to employ molecular oxygen therewith. Nitric oxide is the preferred nitrogen oxide.

The preferred esters of nitrous acid are those esters formed from a saturated monohydric aliphatic alcohol having 1 to 8 carbon atoms, such as a saturated monohydric open-chain aliphatic alcohol or an alicyclic alcohol having 1 to 8 carbon atoms. The most preferred esters of nitrous acid are those prepared from methanol and ethanol. As the alcohol component may be mentioned an aliphatic alcohol such as methanol, ethanol, n-propanol, isopropanol, n-butanol, isobutanol, sec-butanol, tert-butanol, n-amyl alcohol, isoamyl alcohol, hexanol, octanol, etc., and an alicyclic alcohol such as cyclohexanol, methylcyclohexanol, etc. These alcohols may contain therein a substituent such as an alkoxy group which does not inhibit the reaction.

The process by which the ester of nitrous acid is prepared is not narrowly critical so long as the ester of nitrous acid is prepared in the vapor state from gaseous nitrogen oxide and alcohol vapors, and the presence of components deleterious to the oxalate reaction is minimized. Such a component is nitric acid which may adversely affect the supported palladium catalyst employed in the formation of the diester of oxalic acid.

A particularly advantageous process, and preferred in the present invention when the methyl or ethyl esters of nitrous acid are employed, is disclosed in copending application U.S. Ser. No. 227,798 to Arthur R. Doumaux et. al., filed Jan. 23, 1981 and copending application U.S. Ser. No. 239,761, filed concurrently herewith now U.S. Pat. No. 4,353,843 both commonly assigned and both are incorporated herein by reference for their teachings of making methyl and/or ethyl nitrites.

In these applications a novel process is disclosed for the preparation of esters of nitrous acid wherein the process relates particularly to the manufacture of methyl or ethyl nitrite. The process disclosed therein may, in part, be understood more fully by reference to the following equations:

$$2NO + O_2 \rightarrow 2NO_2 \quad (1)$$

$$NO_2 + NO \rightleftharpoons N_2O_3 \quad (2)$$

$$2ROH + N_2O_3 \rightarrow 2RONO + H_2O \quad (3)$$

$$ROH + N_2O_3 \rightarrow RONO + HONO \quad (4)$$

$$ROH + HONO \rightarrow RONO + H_2O \quad (5)$$

$$2NO_2 \rightleftharpoons N_2O_4 \quad (6)$$

$$ROH + N_2O_4 \rightarrow RONO + HNO_3 \quad (7)$$

wherein R is methyl or ethyl.

A goal of the vapor state process disclosed therein is to maximize the production of methyl or ethyl nitrite in the vapor state while minimizing or preferably, essentially eliminating the formation of nitric acid and other unwanted by-products. Thus, it is believed that the product formed in the reaction characterized by equation (2) is employed in equations (3) and (4). Reaction (4) supplies the nitrous acid for reaction (5). That reaction sequence, i.e. (1) through (5), is preferred while the reactions characterized by equations (6) and (7) are to be avoided because of the formation of nitric acid.

In addition, this process discloses, surprisingly, that by providing NO, $NO_2$ and ROH in specific molar ratios that the alkyl nitrite will be formed in high yield with minimal to no formation of nitric acid. To achieve these results the molar ratio of nitric oxide to nitrogen dioxide is provided such that it is greater than one and the molar ratio of alcohol to the combined molar amount of nitric oxide and nitrogen dioxide is greater than one. By thus correlating these two molar ratios the novel process disclosed therein is achieved.

In carrying out the process of U.S. Ser. Nos. 227,798 and 239,761, the source of the reactants is not critical. (This is equally true for other vapor state processes as well.) Nitric oxide may be provided by the decomposition of nitric acid and/or nitrogen dioxide, or may be introduced from an ammonia oxidation unit. The process is generally carried out by introducing nitric oxide and oxygen to form the required amounts of nitrogen dioxide (see equation (1) above). The molar ratio of nitric oxide to nitrogen dioxide is maintained above one in this case by providing nitric oxide and oxygen at a molar ratio of greater than 4 to 1 such that the molar ratio of nitric oxide to the nitrogen dioxide that is formed is greater than 1 (see equation (2) above). In other words, the amount of oxygen converts less than fifty percent (50%) of the nitric oxide to nitrogen dioxide. Also a gaseous medium having the desired ratio of nitric oxide to nitrogen dioxide may be obtained by use of higher oxides of nitrogen ($N_2O_3$, $N_2O_4$, $N_2O_5$, etc.) and to the extent that such higher oxide may be employed to provide a gaseous medium, with or without the additions of molecular oxygen, having a molar ratio of NO to $NO_2$ greater than 1, said higher oxides may be employed herein. In addition, compounds, such as nitrous acid, which can be decomposed or reacted to provide a gaseous medium having a molar ratio of NO to $NO_2$ greater than one may be employed.

As noted above, the process of U.S. Ser. No. 227,798 and Ser. No. 239,761 is preferably carried out by forming the desired molar ratio of NO to $NO_2$ by reacting NO and molecular oxygen at a molar ratio of 4 to 1 or greater. Though the process may be carried out by mixing nitric oxide, molecular oxygen and alcohol (methanol or ethanol) together at the desired molar ratios, such mixing is undesirable because oxygen will oxidize the alcohol to a variety of undesirable reaction by-products with the consequential loss of valuable starting material. Moreover, many of such byproducts, if carried into the oxalate reaction zone would adversely affect the catalyst and contaminate the oxalate ester formed. Therefore, the process is preferably staged such that nitric oxide and molecular oxygen are mixed first and are provided sufficient time for the reaction to consume the oxygen prior to mixing the resulting nitrogen oxide mixture (a mixture having a molar ratio of NO to $NO_2$ greater than 1) with the alcohol. Further this staged addition may reduce the safety problems associated with mixtures of oxygen and alcohols.

As stated in U.S. Ser. Nos. 227,798 and 239,761 the molar ratio of nitric oxide to nitrogen dioxide is greater than 1. Typically the molar ratio (NO to $NO_2$) is from greater than 1 to about 10, most preferably from greater than 1 to about 1.5. The molar ratio of alcohol (methanol or ethanol) to the combined molar amount of nitric oxide and nitrogen dioxide is greater than one. The term "combined molar amount" means the numerical sum of the molar amounts of NO and $NO_2$ that react according to equation (2) above. Typically, the molar ratio of ROH to (NO+$NO_2$) is from greater than 1 to about 10, preferably from greater than 1 to about 2 and most preferably from greater than 1 to about 1.5. The aforementioned molar ratios are thus correlated to optimize the process.

A vapor state alkyl nitrite process is generally carried out in the presence of an inert gaseous diluent to moderate the reaction to preclude the formation of explosive mixtures and prevent the formation of excessive amounts of undesirable by-products. As the inert gaseous diluent, it is preferred to employ nitrogen, carbon dioxide or other inert gaseous compounds. The use of carbon dioxide provides higher heat capacity relative to nitrogen. The inert gaseous diluent is employed in sufficient amounts to provide the aforementioned objectives. The inert gaseous diluent is generally employed in the process such that between about 1 and about 99 mole percent, preferably between about 30 and about 90 mole percent, and most preferably between about 30 and about 70 mole percent comprises inert gaseous diluent.

Further, the alkyl nitrite process is carried out at a temperature sufficient to maintain the nitrogen oxide, alcohol and alkyl nitrite in the vapor state and is typically between about 10° C. and about 300° C., preferably between about 20° C. and about 130° C., and most preferably between about 50° C. and less than about 110° C. The lowest temperature at which the process is conducted is generally determined by the dew point of the alcohol employed and the concentration of the reactants.

The pressure at which the vapor state alkyl nitrite process is carried out is not narrowly critical. It is preferred to employ atmospheric (14.7 psia) or superatmospheric conditions between about 14.7 psia (pounds per square inch absolute) and about 100 psia, and most preferably at between about 20 psia and 60 psia. Pressures less than 14.7 psia may be employed, if desired.

The vapor state alkyl nitrite process is preferably carried out under conditions wherein the concentration of water in the feed to the nitrite forming reaction zone is minimized.

The vapor state alkyl nitrite process may be practiced in almost any commercial reactor (i.e., nitrous ester forming reaction zone) and is generally carried out on a continuous basis by employment of a tubular reactor. The contact time (or residence time) during which the gaseous materials react to form methyl or ethyl nitrite is generally between about 0.1 and about 30 seconds, preferably between about 0.1 and about 2 seconds. Shorter or longer times may be employed depending on the temperature, pressure, molar ratios, gaseous diluent and feed rate employed so long as sufficient time for reaction is provided. In addition, the selection of the reactor geometry of the nitrite forming reaction zone will affect the actual residence time employed.

Because the vapor state alkyl nitrite process is carried out in a continuous manner the feed rate is not narrowly critical, and is selected to satisfy the particular design of the continuous system.

After the ester of nitrous acid (e.g., alkyl nitrite) is formed in the vapor state, the ester in the vapor state is contacted with carbon monoxide in the vapor state in an oxalate forming reaction zone over a palladium supported catalyst containing metallic palladium or salts thereof. The vapor state reaction for the formation of the diesters of oxalic acid is preferably carried out by providing an oxalate forming reaction zone which is without deleterious amounts of water. While some amount of water may be tolerated the amount of water formed in the nitrous ester forming reaction zone is deleterious and a sufficient amount of said water is preferably removed prior to introduction to the oxalate forming reaction zone. This may be accomplished by use of a water condenser (in conjunction with a vapor-liquid separator) after alkyl nitrite formation or by the use of any other suitable dehydration process. The amount of water which is deleterious to the vapor state reaction for the formation of diesters of oxalic acid is determined, in part, by the selection of ester of nitrous acid, temperature, pressure, etc. In general, a deleterious amount of water is that amount of water which causes a significant change in the rate and selectivity to oxalate as compared to the rate and selectivity when a non-deleterious amount is present. The amount of water in the oxalate forming reaction zone is preferably less than about 5.0 mole percent, more preferably less than about 2.0 mole percent and most preferably less than about 1.0 mole percent.

Carbon monoxide to be used in oxalate formation by the process of this invention may be obtained from any conventional source. It may be pure or be contaminated with small amounts of hydrogen and/or inert hydrocarbons, or it may be diluted with an inert gas, such as nitrogen, carbon dioxide and the like. The concentration of carbon monoxide in the reaction zone is not narrowly critical and may vary over a wide range between about 1 and about 99 mole percent. Typically, the concentration of carbon monoxide is in the range of between about 10 percent and about 95 mole percent, wherein the actual concentration of carbon monoxide in the reaction mixture will depend on the alkyl nitrite employed and its concentration, the catalyst employed in the process, concentration of inert gaseous diluent and the selected process conditions. The molar concentration of carbon monoxide is preferably selected to provide an excess of carbon monoxide over the ester of nitrous acid so that the molar ratio of carbon monoxide is between about 2 and about 20.

The reaction for the formation of the diester of oxalic acid is carried out in the presence of an inert gaseous diluent to moderate the reaction, and in part, to preclude the formation of explosive mixtures and prevent the formation of excessive amounts of undesirable by-products. When carrying out the continuous process of the present invention some amount of inert gaseous diluent is present in the gaseous stream containing alkyl nitrite. Additional inert gaseous diluent may be added concurrently with the carbon monoxide or at some time before or after the addition of carbon monoxide. As the inert gaseous diluent, it is preferred to employ nitrogen, carbon dioxide or other gaseous compounds inert in the reaction. The use of carbon dioxide provides high molar heat capacity relative to nitrogen. The total amount of inert gaseous diluent present in the oxalate forming reaction zone is that amount sufficient to provide the aforementioned objectives, and is such that the concentration of inert gaseous diluent is between about 1 and about 99 mole percent. Typically, the concentration of inert gaseous diluent is between about 0 (zero) percent and about 90 mole percent, wherein the actual concentration employed is chosen as before discussed with respect to the concentration of carbon monoxide.

The vapor state process for forming the diester of oxalic acid is generally carried out at a temperature of between about 50° C. and about 200° C. and preferably between about 75° C. and about 150° C.

The formation of diester of oxalic acid is generally carried out under atmospheric or super-atmospheric pressure, preferably such that the pressure is between about atmospheric (14.7 psia) and about 100 psia and more preferably between about 15 psia and about 60 psia. Pressures less than 14.7 psia may be employed, if desired.

The formation of the diester of oxalic acid is preferably carried out in a reactor with a fixed bed or dynamic bed, such as a fluidized bed, of the catalyst. The particulate catalyst may be diluted by particles of inert carrier or other inert materials, to enhance control over the reaction temperature.

The contact or residence time during which the diester of oxalic acid is formed is not narrowly critical and generally less than about 30 seconds and preferably between about 0.05 and about 10 seconds such that the time is sufficient for reaction.

The supported palladium catalyst employed in the process is preferably formed with a non-acidic carrier with a surface area less than 10 square meters per gram. However, the catalysts may be formed with carriers such as activated charcoal, alpha or gamma alumina, silica, diatomaceous earth, pumice, and molecular sieves.

U.S. Pat. No. 4,038,175 discloses a hydrogenation process which employs palladium or platinum metal dispersed on the surface of an alpha-alumina support. The description beginning at column 3, line 42 to column 4, line 24, and the description at column 5, line 2 to column 8, line 22, relating to the description of palladium supported on the carrier alpha-alumina and the process for preparing the catalyst disclosed therein are incorporated herein by reference.

A preferred catalyst carrier for use in the preparation of diesters of oxalic acid is disclosed in commonly assigned U.S. applications, Ser. Nos. 227,640, filed Jan. 23, 1981, and 239,762, filed 3-12-81, both to Lou Kapicak, et al., the latter application filed concurrently herewith, and both incorporated herein by reference. Exemplary of such a catalyst carrier is alpha-alumina.

The catalyst carrier employed in U.S. Ser. Nos. 227,640 and 239,762 in practicing the invention thereof, may be selected from conventional, porous, refractory materials which are essentially inert to the reactants and products at reaction conditions. These materials are generally labelled as "macroporous" and consist of porous materials having low surface area of less than about 10 m$^2$/g (square meters per gm) and preferably less than 5 m$^2$/g and greater than 0.001 m$^2$/g. The surface area is measured by the conventional B.E.T. method described by Brunauer, S., Emmet, P., and Teller, E., in J. Am. Chem. Soc., Vol. 60, pp. 309–16, (1938). The carrier may be shaped in the form of pellets, spheres, rings, cylindrical rings; desirably a shape which provides the optimum gas flow for the selected reactor.

The amount of palladium deposited on the carrier is not narrowly critical and is in the range of between about 0.001 to 10% by weight, preferably between 0.01 to about 5% by weight and most preferably between about 0.05 to 2% by weight, calculated as metallic palladium.

The particle size of palladium metal or salt thereof deposited upon the carrier and the dispersion of the palladium are a function of the catalyst preparation procedure employed. Thus, the particular choice of solvent and/or complexing agent, palladium salt, heat treatment conditions and catalyst carrier may effect, to varying degrees, the size of the resulting palladium particle. For catalysts of general interest for the production of diesters of oxalic acid, a distribution of palladium particle sizes below about 10,000 Angstroms is preferred. However, the role of particle size of the palladium catalyst upon the effectiveness of the catalyst in making the diesters of oxalic acid is not clearly understood. In view of the fact that the palladium particles may migrate on the surface of the catalyst when used in the catalytic reaction resulting in a marked change in their size and shape, palladium particle size may or may not be a significant factor in affecting catalytic performance. Further, the dispersion of the palladium catalyst may be determinant in optimizing the production of oxalic acid diester, and even though such dispersion is not clearly understood at present a high dispersion of palladium particles is considered to be preferred.

The process of the invention is an "integrated" process wherein the term "integrated" is meant to refer to a process wherein the vapor state formation of alkyl nitrite and the vapor state formation of dialkyl oxalate ester are coupled and correlated so as to provide an overall vapor state process that may be continuous or cyclic in operation. The use of a continuous vapor state process comprising the coupling of the formation of alkyl nitrite and the formation of dialkyl oxalate is advantageous because the process minimizes the formation of by-products, achieves enhanced ease of operation and enhances production efficiencies.

DESCRIPTION OF THE FIGURES

In carrying out the process of this invention it is important to maintain both the formation of alkyl nitrite and the formation of diester of oxalic acid in the vapor state. Such an integrated vapor state process is shown in FIGS. 1 and 2 wherein the input and output of the nitrite reactor and the input and output of oxalate reactor are correlated to provide an integrated and optimized process in the vapor state.

Figure 1:
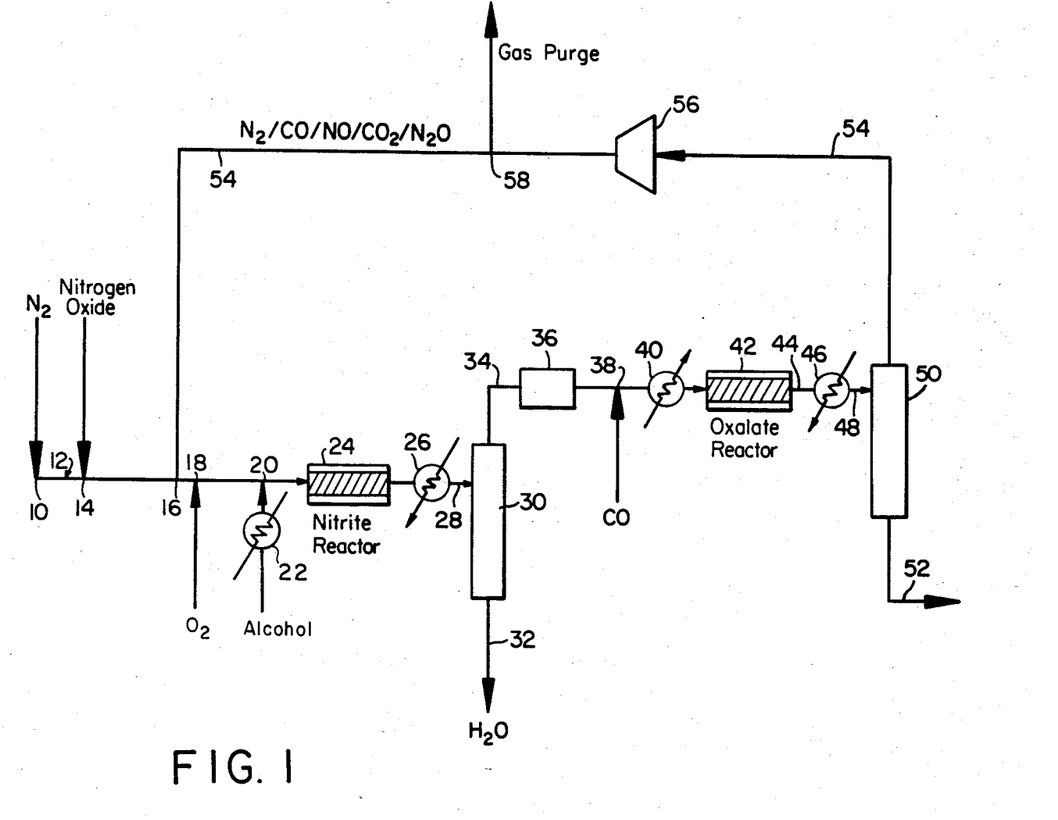
FIG. 1 depicts schematically an integrated vapor state process suitable for the present invention.
Figure 2:
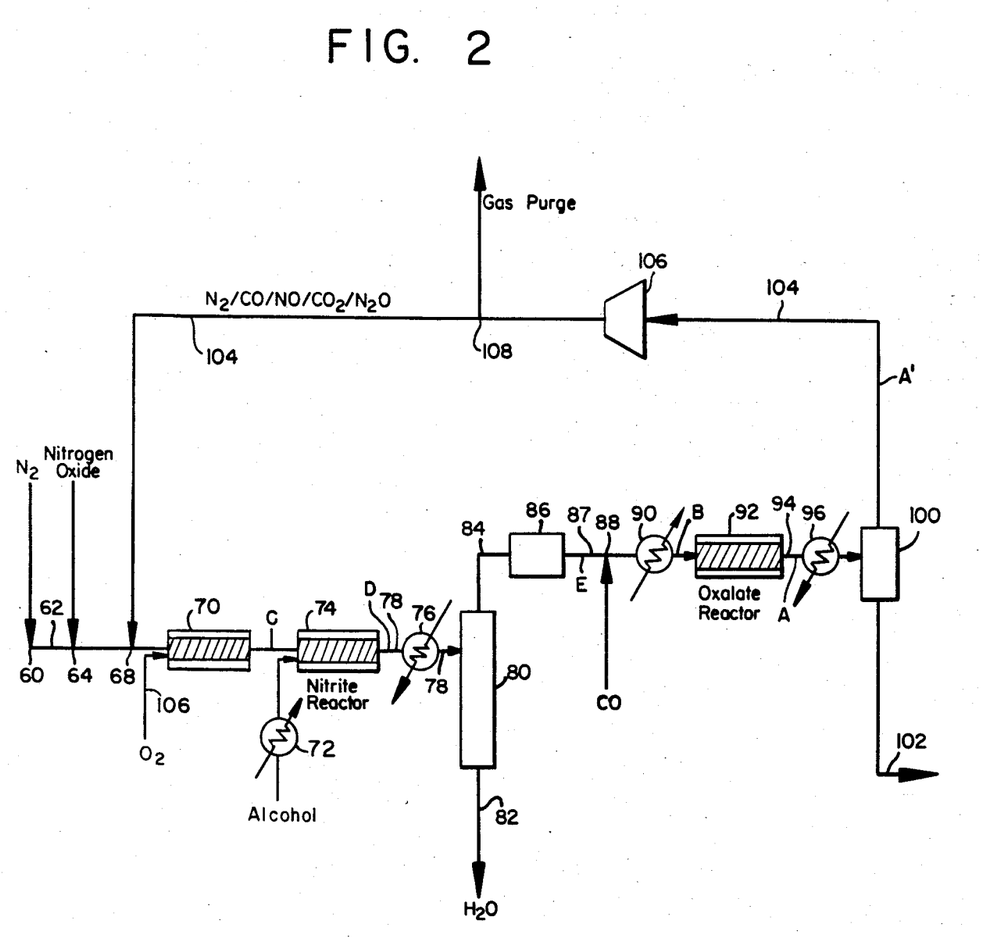
FIG. 2 schematically depicts an apparatus for carrying out the invention.

FIG. 1 depicts schematically an integrated vapor state process suitable for use in practicing the invention. Referring to FIG. 1, inert diluent (designated herein as nitrogen) is introduced at 10 of line 12, and admixes with a nitrogen oxide (in this case nitric oxide) at 14. The order of introduction is not critical. The $N_2$/nitrogen oxide mixture at 14 is provided to the process as make-up to replace, as required, routine losses of nitrogen and nitrogen oxide, which may occur in carrying out the process. Molecular oxygen is added at 18 when its addition is required to form nitrogen dioxide for the process. Alternatively, molecular oxygen may be added to the recycle gas in line 54 (not shown). The addition of molecular oxygen to the process is provided so that oxygen is added to the nitrogen oxide prior to the introduction of alcohol to prevent oxidation of alcohol and thus prevent the formation of deleterious by-products and to avoid the formation of flammable mixtures. Alcohol is vaporized in heat exchanger (vaporizer) 22 and is added to the mixture of line 12 at 20. The recycled gas in line 54 is introduced into line 12 at point 16.

The mixture in line 12 is maintained in the vapor state and is introduced into nitrite reactor 24 (nitrous ester forming reaction zone) at a specified temperature and pressure, as discussed above, wherein the ester of nitrous acid is formed. The ester of nitrous acid exits nitrite reactor 24, passes to heat exchanger 26 wherein it is sufficiently cooled for condensation of water and unreacted alcohol as necessary, and passes via line 28 to vapor-liquid separator 30 from which water and unreacted alcohol are removed through line 32.

The gaseous mixture containing the ester of nitrous acid passes from vapor-liquid separator 30 by way of line 34 through a purification process 36, if necessary, for removal of residual water and trace impurities, so that the concentration of undesired materials is controlled at a predetermined level. The ester of nitrous acid then is contacted with carbon monoxide introduced at 38 prior to heat exchanger (heater) 40. The mixture of carbon monoxide and ester of nitrous acid are heated in heat exchanger 40 to about the desired inlet temperature of oxalate reactor 42. The mixture is introduced to oxalate reactor 42 (oxalate forming reaction zone) wherein is contained the supported palladium catalyst at a specified temperature and pressure, as previous discussed. The stream exiting oxalate reactor 42 through line 44 contains the formed diester of oxalic acid, gaseous components, such as $N_2$, CO, NO, $CO_2$, $N_2O$, and the like, and a minor amount of by-products.

The stream in line 44 passes through heat exchanger 46 wherein the stream is cooled for condensation of the oxalate product prior to introduction to vapor-liquid separator 50 wherein the liquid oxalate product is collected and removed as product through line 52.

The effluent gases from vapor liquid separator 50 exit the separator through line 54 and are recycled to incoming line 12 through compressor 56 to point 16. Compressor 56 is provided to adjust the pressures between the exit of oxalate reactor 42 and the inlet pressure of nitrite reactor 24. A gas purge is provided at point 58 of line 54 to allow for control of the components in the recycle gas (effluent gas from vapor-liquid separator 50) provided to nitrite reactor 24 and to provide a control on the amount of inert gas in the process, particularly to prevent build up of inerts such as carbon dioxide. It has been found that correlation of the composition of the recycling gas for nitrite reactor 24 is significant in providing an optimized integrated process.

As will be obvious to one skilled in the art, when a continuous process is carried out as set forth in FIG. 1, the inert gaseous diluent introduced through line 10 and the nitrogen oxide introduced through line 12 are provided as required to make up losses occurring in the process, due to routine losses and to losses resulting from the use of the gas purge at 58.

For examples 1 to 7, hereinafter, reference will be made to FIG. 2 which schematically depicts an apparatus for carrying out the process of the present invention. The process is preferably carried out in a continuous manner in a series of elongated tubular zones, although alternative zone geometries may be employed. The material of construction should be such that it is inert during the reaction and the fabrication of the equipment should be able to withstand the reaction temperatures and pressures. The reaction zones may be fitted with internal or external heat exchanger(s) to thus control temperature, and to prevent any possible "run-away" reaction temperatures due to the exothermic nature of any of the reactions. In FIG. 2, no mixing apparatus is shown for the various gaseous components at their various points of introduction since mixing is generally achieved through the turbulent condition present at the point of introduction of the process reactant. Mixing induced by vibration, shaker, stirrer, rotation, oscillation, ultrasonic, etc., are all illustrative of the types of agitation means which may be employed to mix the gaseous component in the several lines and the nitrite reactor and oxalate reactor. Such means are available and well-known to the art. The supported palladium catalyst employed in the oxalate forming reaction zone is generally introduced into the oxalate reactor prior to the start of the process but may be provided continuously to the process as in the case of a dynamic reactor bed, particularly a fluidized bed, wherein new catalyst is introduced into the oxalate reactor during the course of the process. Means to introduce and/or adjust the reactants (i.e., gaseous process components), either intermittently or continuously, in the reaction zone during the course of the reaction can be conveniently utilized in the process especially to maintain the desired molar ratios of the reactants in the nitrous acid ester forming zone and the oxalate forming zone.

The operative conditions, e.g., temperature, pressure, relative molar ratios of reactants, may be adjusted to optimize the conversion to the desired product and/or the economics of the process. In the following description of FIG. 2 the described conditions are for the preparation of the ethyl ester of nitrous acid and for diethyl oxalate and are not intended to limit but serve only to illustrate the conditions which may be used for the ethyl ester of nitrous acid in forming diethyl oxalate.

With respect to FIG. 2, inert gaseous diluent (designated in FIG. 2 as nitrogen) is introduced at 60 of line 62 and admixes with a nitrogen oxide (nitric oxide in the instant case) at 64 of line 62. (Mixing here and in subsequent process steps may be by means as abovedescribed.) The order of introduction is not critical. In the continuous process the $N_2$/nitrogen oxide mixture at point 64 is provided as required to makeup any losses, e.g., by purging of nitrogen or nitrogen oxide from the cycle gas. This "make-up" gas is combined with recycle stream 104 at 68. Molecular oxygen is added via line 106 to nitrogen oxide generator 70 as required. The addition of molecular oxygen to nitrogen oxide generator 70 is provided so that the addition of oxygen is prior to the introduction of ethanol and is essentially consumed by reaction with nitric oxide so as to prevent the possible oxidation of the ethanol by oxygen, the resultant formation of deleterious by-products and to avoid the formation of flammable mixtures. Ethanol is added to nitrite reactor 74 after having been heated to the vapor state by heat exchanger 72. Additional heat exchangers (not shown) may be provided to adjust the stream temperatures to the desired inlet temperature of nitrite reactor 74.

The stream in line 62 is also introduced to nitrite reactor 74 (nitrous acid ester forming reaction zone), shown as a tubular reactor, at a specified temperature and pressure (between about 50° C. and about 110° C. and between about 1 and about 3 atmospheres for ethyl nitrite formation) wherein ethyl nitrite is formed. Alternatively the nitrite reactor may be as described in U.S. Ser. No. 227,798, filed Jan. 23, 1981 pending or U.S. Ser. No. 239,761 filed 3-12-81, now U.S. Pat. No. 4,616,093, both applications being discussed above. The effluent (containing ethyl nitrite) from nitrite reactor 74 passes via line 78 to heat exchanger 76 where it is sufficiently cooled for condensation of water and unreacted alcohol, as necessary, prior to introduction to vapor-liquid separator 80 from which condensed water and unreacted alcohol are removed through line 82. Vapor-liquid separator 80 generally comprises a wide tubular body with a width greater than line 78 to reduce gas flow rate. Alternatively, the vapor-liquid separator may comprise a tubular zone with internal mesh or struts or a pot having a tangential entrance for incoming gases causing swirling of gases.

The effluent (containing ethyl nitrite) is removed by way of line 84 and passes through a purification process tank 86, if necessary, for removal of residual water and trace impurities, so that the concentration of undesired materials is controlled at a predetermined level. The ethyl nitrite in line 87 is then admixed with carbon monoxide at 88 prior to heat exchanger (heater) 90 wherein the mixture is heated to about the desired inlet temperature of oxalate reactor 92. The formation of diethyl oxalate takes place in oxalate reactor 92 (oxalate forming reaction zone) at a specified temperature and pressure (e.g., at a temperature of between about 110° C. and about 130° C. and between about 1 and about 2 atmospheres for the formation of diethyl oxalate). The stream exiting oxalate reactor 92 via line 94 contains diethyl oxalate, minor amounts of by-products, unreacted CO, inert diluent (e.g., nitrogen), and other gaseous components, such as NO, $CO_2$, $N_2O$, and the like.

The stream in line 94 passes through heat exchanger 96 wherein it is cooled for condensation of the oxalate product prior to introduction to vapor-liquid separator 100 wherein the liquid oxalate product is collected and removed through line 102 for subsequent treatment processes, if any, as desired.

The effluent gases from vapor-liquid separator 100 exit the separator through line 104 and are recycled to incoming line 62 through compressor 106. Compressor 106 is provided to increase the pressure in line 104 to the desired pressure in nitrogen oxide generator 70 and may comprise a blower-type compressor or a pump-type compressor. The selection of the compressor is dependent on the pressure differential between the operating pressures of nitrogen oxide generator 70 and oxalate reactor 92, such selection being within the skill of the practitioner once the pressure differential is known. A gas purge is provided at 108 in line 104 to allow for control of components in the recycle stream, provide for control of the amount of inert gaseous diluent present in the process and provide a means for controlling the pressure in the process. Particularly, the gas purge is provided to prevent the build up inerts and/or by-products beyond a predetermined level. By carefully correlating the recycled effluent gases in line 104, the reactions in nitrogen oxide generator 70, and nitrite reactor 74 may be optimized.

EXAMPLES 1–7

The several examples set forth hereinafter are understood by reference to FIG. 2 and by reference to the mole percent of the dialkyl oxalate (diethyl oxalate is the dialkyl oxalate in each example), alkyl nitrite (ethyl nitrite is alkyl nitrite in each example), carbon monoxide, nitrogen oxide (nitric oxide is the nitrogen oxide in each example), inert diluent (nitrogen is the inert diluent in each example), oxygen, alcohol (ethanol is the alcohol in each example) and water; and such mole values (given as the mole percent) are set forth by reference to the composition of streams 94, 84, 62, 78 and 87 as designated in FIG. 2. wherein these streams are also designated by the letters A, B, C, D and E, respectively. It is noted that the composition of stream 104 at A' of FIG. 2 is simply the composition at A less the condensed liquid in line 102.

In each example the following is the molar ratio of carbon monoxide to ethyl nitrite in the diethyl oxalate forming reaction zone:

TABLE I

| Example | Carbon Monoxide to Ethyl Nitrite Ratio |
|---------|----------------------------------------|
| 1 | 4:1 |
| 2 | 8:1 |
| 3 | 4:1 |
| 4 | 2:1 |
| 5 | 1.87:1 |
| 6 | 1.75:1 |
| 7 | 4:1 |

In examples 1 to 7 the catalyst is a 2.0 percent palladium catalyst on an alpha-alumina carrier having the following chemical composition and physical properties:

|  | Wt. Percent |
|---|---|
| Chemical Composition | |
| Alpha-Alumina | 98.5 |
| Silicon Dioxide | 0.74 |
| Calcium Oxide | 0.22 |
| Sodium Oxide | 0.16 |
| Ferric Oxide | 0.14 |
| Potassium Oxide | 0.04 |
| Magnesium Oxide | 0.03 |
| Physical Properties | |
| Surface Area (1) | ~0.03 m$^2$/g |
| Pore Volume (2) (or water adsorption) | ~0.50 cc/g |
| Packing Density (3) | 0.70 g/ml |
| Median Pore Diameter (4) | 21 microns |

-continued

| Pore Size Distribution, Percent Total Pore Volume (4) | |
|---|---|
| Pore Size, Microns | TPV (Percent) |
| 0.1–1.0 | 1.5 |
| 1.0–10.0 | 38.5 |
| 10.0–30.0 | 20.0 |
| 30–100 | 21.0 |
| >100 | 8.0 |

(1) Method of measurement described in "Adsorption, Surface Area and Porosity", S. J. Gregg and K. S. W. Sing, Academic Press (1967), pages 316–321.
(2) Method of measurement as described in ASTM C20-46.
(3) Calculated value based on conventional measurement of the weight of the carrier in a known volume container.
(4) Method of measurement described in "Application of Mercury Penetration to Materials Analysis", C. Orr Jr., Powder Technology. Vol. 3, pp. 117–123 (1970).

In Examples 1–7, referring to FIG. 2, the temperature of nitrite reactor 74, is between about 50° C. and about 110° C. and the pressure is between about 1 and about 3 atmospheres. The temperature of oxalate reactor 92 is between about 110° C. and about 130° C. with a pressure of between about 1 and about 2 atmospheres. Nitrite reactor 74 is as shown in FIG. 1 of U.S. Ser. No. 227,798 and oxalate reactor 92 is a 4 foot long No. 304 stainless steel tube having an inside diameter of ½ inch with seven sheathed thermocouples placed every 6 inches in a gravity packed catalyst bed. Vapor-liquid separators 80 and 100 and heat exchangers 72 and 90 are of standard design. The various lines are of ¼ inch outside diameter (0.185 inside diameter) stainless steel tubing. Compressor 106 is a pump-type compressor.

Examples 1 to 7 are set forth in Tables II to VIII, respectively, as follows:

TABLE II[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 2 | — | — | — | — |
| Carbon monoxide | 12 | 15.69 | 11.54 | 11.88 | 12.24 |
| Nitric oxide | 5 | 0.98 | 4.51 | 0.99 | 1.02 |
| Nitrogen | 81 | 79.41 | 77.88 | 80.20 | 82.66 |
| Oxygen[4] | — | — | 0.96 | — | — |
| Ethyl nitrite | — | 3.92 | — | 3.96 | 4.8 |
| Ethanol[3] | — | — | 4.81 | 0.97 | — |
| Water | — | — | — | 1.98 | — |

[1]Example 1.
[2]Mole percent based on total moles in stream over a one hour period.
[3]Alcohol recycled to oxalate reactor.
[4]Oxygen feed to line 106.

TABLE III[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 2 | — | — | — | — |
| Carbon monoxide | 28 | 31.37 | 26.92 | 27.72 | 28.5 |
| Nitric oxide | 5 | 0.98 | 4.81 | 0.99 | 1.0 |
| Nitrogen[3] | 65 | 63.73 | 62.50 | 64.36 | 66.3 |
| Oxygen[4] | — | — | 0.96 | — | — |
| Ethyl nitrite | — | 3.92 | — | 3.96 | 4 |
| Ethanol | — | — | 4.81 | 0.97 | — |
| Water | — | — | — | 1.98 | — |

[1]Example 2.
[2]Mole percent based on total moles in said stream over a one hour period.
[3]Nitrogen as the inert.
[4]Oxygen feed to line 106.

TABLE IV[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 8 | — | — | — | — |
| Carbon monoxide | 48 | 59.26 | 41.38 | 46.15 | 52.17 |
| Nitric oxide | 20 | 3.70 | 17.24 | 3.85 | 4.35 |
| Nitrogen[3,4] | 24 | 22.22 | 20.69 | 23.08 | 26.09 |
| Oxygen[5] | — | — | 3.45 | — | — |
| Ethyl nitrite | — | 14.82 | — | 15.38 | 17.39 |
| Ethyl alcohol | — | — | 17.24 | 3.85 | — |
| Water | — | — | — | 7.69 | — |

[1] Example 3.
[2] Mole percent based on total moles in stream over a one hour period.
[3] Inert is nitrogen.
[4] Use of only 24 mole percent inert is close to presenting a safety hazard.
[5] Oxygen feed to line 106.

TABLE V[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 8 | — | — | — | — |
| Carbon monoxide | 16 | 29.63 | 13.79 | 15.38 | 17.39 |
| Nitric oxide | 20 | 3.70 | 17.24 | 3.85 | 4.35 |
| Nitrogen[3] | 56 | 51.85 | 48.28 | 53.85 | 60.87 |
| Oxygen[4] | — | — | 3.45 | — | — |
| Ethyl nitrite | — | 14.82 | — | 15.38 | 17.39 |
| Ethanol | — | — | 17.24 | 3.85 | — |
| Water | — | — | — | 7.69 | — |

[1] Example 4.
[2] Mole percent based on total moles in stream over a one hour period.
[3] Nitrogen is the inert gas.
[4] Oxygen feed to line 106.

TABLE VI[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 8 | — | — | — | — |
| Carbon monoxide | 14 | 27.78 | 12.04 | 13.46 | 15.22 |
| Nitric oxide | 20 | 3.70 | 17.24 | 3.85 | 4.35 |
| Inert[3] | 58 | 53.7 | 50.0 | 55.77 | 63.04 |
| Oxygen[4] | — | — | 3.45 | — | — |
| Ethyl nitrite | — | 14.82 | — | 15.38 | 17.39 |
| Ethanol | — | — | 17.24 | 3.85 | — |
| Water | — | — | — | 7.69 | — |

[1] Example 5.
[2] Mole percent based on total moles in stream over a one hour period.
[3] Nitrogen is the inert gas.
[4] Oxygen feed to line 106.

TABLE VII[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 8 | — | — | — | — |
| Carbon monoxide | 12 | 25.93 | 10.71 | 12 | 13.04 |
| Nitric oxide | 20 | 3.70 | 17.86 | 4 | 4.35 |
| Nitrogen[3] | 56 | 51.85 | 50 | 56 | 60.87 |
| Oxygen[5] | — | — | 3.57 | — | — |
| Ethyl nitrite | — | 14.82 | — | 16 | 17.39 |
| Ethanol[4] | 4 | 3.7 | 17.86 | 4 | 4.35 |

TABLE VII[1,2]-continued

|  | STREAM A Mole (%) | STREAM B Mole (%) | STREAM C Mole (%) | STREAM D Mole (%) | STREAM E Mole (%) |
|---|---|---|---|---|---|
| Water | — | — | — | — | — |

[1]Example 6.
[2]Mole percent based on total moles in stream over a one hour period.
[3]Inert is nitrogen.
[4]Ethanol recycled to oxalate reactor.
[5]Oxygen feed to line 106.

TABLE VIII[1,2]

|  | STREAM A Mole (%) | STREAM B Mole (%) | STREAM C Mole (%) | STREAM D Mole (%) | STREAM E Mole (%) |
|---|---|---|---|---|---|
| Diethyl oxalate | 4.76 | — | — | — | — |
| Carbon monoxide | 28.57 | 36.36 | 26.09 | 27.91 | 30.0 |
| Nitric oxide | 11.90 | 2.27 | 10.87 | 2.32 | 2.5 |
| Nitrogen[3] | 54.76 | 52.27 | 20 | 53.49 | 57.5 |
| Oxygen[5] | — | — | 2.17 | 9.30 | — |
| Ethyl nitrite | — | 9.09 | — | 2.32 | 10.0 |
| Ethanol[4] | — | — | 10.87 | 4.65 | — |
| Water | — | — | — | — | — |

[1]Example 7.
[2]Mole percent based on total moles in stream over a one hour period.
[3]Inert is nitrogen.
[4]Alcohol recycled to oxalate reactor.
[5]Oxygen feed to line 106.

What is claimed is:

1. A vapor state process for the preparation of diesters of oxalic acid which comprises:
   (a) contacting a nitrogen oxide and a saturated monohydric aliphatic alcohol containing 1 to about 8 carbon atoms in the vapor state in a nitrite forming reaction zone at a temperature between about 10° C. and about 300° C., for a sufficient time to form an ester of nitrous acid; and
   (b) maintaining the ester of nitrous acid in the vapor state and contacting said ester of nitrous acid, free of deleterious amounts of water, with carbon monoxide in the vapor state in an oxalate forming reaction zone at a temperature of between about 50° C. and about 200° C., over a supported palladium catalyst containing metallic palladium or a salt thereof for a period of time sufficient to produce the diester of oxalic acid and recovering the diester of oxalic acid from the oxalate forming reaction zone.

2. The process of claim 1 wherein the alcohol is either methanol or ethanol.

3. The process of claim 1 wherein the process is carried out at atmospheric (14.7 psia) pressure or superatmospheric pressure.

4. The process of claim 1 wherein the temperature at which said ester of nitrous acid is contacted with carbon monoxide in step (b) is between about 75° C. and about 150° C.

5. The process of claim 1 wherein there is present an inert gaseous diluent in both reaction zones.

6. The process of claim 5 wherein the gaseous inert diluent is selected from the group consisting of nitrogen, carbon dioxide and mixtures thereof.

7. The process of claim 1 wherein the supported palladium catalyst is formed with a non-acid carrier having a surface area no greater than 10 square meters per gram of carrier.

8. The process of claim 7 wherein the carrier is an alpha-alumina.

9. The process of claim 8 wherein the process is carried out such that the pressure in steps (a) and (b) is atmospheric (14.7 psia) pressure or super-atmospheric pressure.

10. The process of claim 9 wherein the pressure in step (b) at which the ester of nitrous acid and carbon monoxide are contacted over said supported palladium catalyst is between about atmospheric (14.7 psia) pressure and about 100 psia.

11. The process of claim 9 wherein the pressure is between about 15 psia and about 60 psia.

12. A continuous vapor state process for the preparation of diesters of oxalic acid which comprises the steps of:
   (a) making an ester of nitrous acid in the vapor state by reacting a nitrogen oxide, oxygen, and a saturated monohydric aliphatic alcohol containing 1 to about 8 carbon atoms, at a temperature sufficient to maintain said nitrogen oxide, oxygen, alcohol and ester of nitrous acid in the vapor state in a nitrous ester forming reaction zone under atmospheric (14.7 psia) or superatmospheric pressure for a period of time sufficient to form said ester of nitrous acid;
   (b) introducing said ester of nitrous acid from step (a), while maintaining said ester of nitrous acid in the vapor state, free of deleterious amounts of water, into an oxalate forming reaction zone wherein said ester of nitrous acid is contacted with carbon monoxide in the vapor state under atmospheric (14.7 psia) or superatmospheric pressure over a palladium supported catalyst containing metallic palladium or a salt thereof at a temperature of between about 50° C. and about 200° C. and for a period of time sufficient to produce the diester of oxalic acid and nitrogen oxide containing effluent; and
   (c) recovering the dialkyl oxalate formed in step (b) and recycling at least a portion of the nitrogen oxide containing effluent of step (b) to step (a).

13. A continuous vapor state process, for the preparation of the methyl or ethyl diesters of oxalic acid wherein the process comprises:
  (a) making the methyl or ethyl ester of nitrous acid from methanol or ethanol, respectively, which comprises reacting in a reaction zone a molar amount of a nitrogen oxide composition containing a nitric oxide to nitrogen dioxide molar ratio of greater than 1, with a molar amount of vaporized methanol or ethanol wherein the molar ratio of methanol or ethanol to the combined molar amount of nitric oxide and nitrogen dioxide is greater than one, in the presence of an inert gaseous diluent for said reaction, at a temperature between about 10° C. and about 130° C. for a period of time sufficient to form said methyl or ethyl ester of nitrous acid;
  (b) contacting said methyl or ethyl ester of nitrous acid of step (a) after removing deleterious amounts of water therefrom, in the vapor state with carbon monoxide in the presence of a palladium supported catalyst comprising metallic palladium or a salt thereof on a non-acidic carrier having a surface area less than about 10 $m^2/g$ at a temperature of between about 50° C. and about 200° C. such that methyl or ethyl diester of oxalic acid and a nitrogen oxide containing effluent are formed; and
  (c) recovering diester from step (b) and recycling at least a portion of the nitrogen oxide containing effluent of step (b) to step (a).

14. The process of claim 1 wherein deleterious amounts of water are removed from said ester of nitrous acid prior to step (b).

15. The process of claim 1 or 12 wherein deleterious amounts of water are removed from said ester of nitrous acid prior to step (b).

16. The process of claim 13 wherein the process is carried out such that the pressure in steps (a) and (b) are atmospheric (14.7 psia) pressure or superatmospheric pressure.

17. The process of claim 16 wherein the pressure is superatmospheric.

18. The process of claim 17 wherein the pressure in step (b) is between about 20 psia and about 60 psia.

19. The process of claim 1 wherein the temperature in step (a) is between about 50° C. and about 110° C.

20. The process of claim 1, 12 or 13 wherein the carrier for said supported palladium catalyst is an alpha-alumina.

21. The process of claim 1 wherein the process is a continuous process.

22. The process of claim 15 wherein the amount of water in step (b) is less than about 5.0 percent by weight.

23. The process of claim 22 wherein the amount of water is less than about 2.0% by weight.

24. The process of claim 23 wherein the amount of water is less than about 1.0% by weight.

25. A continuous process for the preparation of diesters of oxalic acid which comprises the steps of:
  (a) making an ester of nitrous acid by reacting a nitrogen oxide, oxygen, and a saturated monohydric aliphatic alcohol containing 1 to about 8 carbon atoms;
  (b) introducing said ester of nitrous acid from step (a) in the vapor state into an oxalate forming reaction zone wherein said ester of nitrous acid is contacted with carbon monoxide under atmospheric (14.7 psia) or superatmospheric pressure over a supported palladium catalyst containing metallic palladium or a salt thereof supported on a non-acid, alpha-alumina carrier having a surface area no greater than 10 square meters per gram of carrier at a temperature of between about 50° C. and about 200° C. and for a period of time sufficient to produce the diester of oxalic acid and a nitrogen oxide-containing effluent; and
  (c) recovering the dialkyl oxalate formed in step (b) and recycling at least a portion of the nitrogen oxide-containing effluent of step (b) to step (a).

26. The process of claim 25 wherein the process is carried out in the vapor state.

* * * * *